United States Patent
Gazonnet et al.

(10) Patent No.: US 12,133,655 B2
(45) Date of Patent: Nov. 5, 2024

(54) REUSABLE SURGICAL GUIDE FOR OSTEOSYNTHESIS SURGERY IN PARTICULAR OF THE HALLUX VALGUS

(71) Applicant: NOVASTEP, Rennes (FR)

(72) Inventors: Lilian Gazonnet, Montrevel en Bresse (FR); Adrien Bousquet, La Meziere (FR); Loïc Girod, Goven (FR); Brian Schauer, Huntersville, NC (US); Brian Loder, Clinton Township, MI (US); Tristan Meusnier, Saint Etienne (FR); Peter Lam, Sydney (AU); Oliver Schipper, Arlington, VA (US); Holly Johnson, Wayland, MA (US)

(73) Assignee: NOVASTEP, Rennes (FR)

( * ) Notice: Subject to any disclaimer, the term of this patent is extended or adjusted under 35 U.S.C. 154(b) by 334 days.

(21) Appl. No.: 17/126,608

(22) Filed: Dec. 18, 2020

(65) Prior Publication Data
US 2022/0192685 A1  Jun. 23, 2022

(51) Int. Cl.
*A61B 17/17* (2006.01)
*A61B 17/88* (2006.01)
A61B 17/00 (2006.01)
A61B 17/90 (2006.01)

(52) U.S. Cl.
CPC ...... *A61B 17/1739* (2013.01); *A61B 17/8861* (2013.01); *A61B 2017/00367* (2013.01); *A61B 17/90* (2021.08)

(58) Field of Classification Search
CPC . A61B 17/1697; A61B 17/90; A61B 17/8861; A61B 17/1775; A61B 17/1782; A61B 17/1739; A61B 17/1721; A61B 17/1725; A61B 17/1717; A61B 17/1714; A61B 17/1764
See application file for complete search history.

(56) References Cited

U.S. PATENT DOCUMENTS 5,891,150 A * 4/1999 Chan ................. A61B 17/1714
606/98
6,860,883 B2 * 3/2005 Janowski ............. A61B 17/645
606/56

(Continued)

FOREIGN PATENT DOCUMENTS

WO   2017/040843 A1   3/2017

OTHER PUBLICATIONS

McMaster-Carr, "Metal Worms and Worm Gears", https://www.mcmaster.com/worm-screws/, accessed Mar. 14, 2023 (Year: 2023).*

*Primary Examiner* — Amy R Sipp
(74) *Attorney, Agent, or Firm* — Oliff PLC (57) ABSTRACT

The present invention concerns a reusable surgical guide for osteosynthesis surgery, forming an aimer for guiding and inserting axial wires into bone portions; said guide comprises a grip constituted by a head extending at the upper end of a base, a trigger adapted to be displaced in a first slide formed in the head of the grip and whose distal end is provided with a through hole for the insertion of a wire, a blade secured to the distal end of the head of the grip, under the trigger, and a so-called aiming piece adapted to be displaced in a second slide formed in the base of the grip, said aiming piece comprising at the distal end thereof means for supporting at least one wire.

18 Claims, 11 Drawing Sheets

(56) References Cited

U.S. PATENT DOCUMENTS

| | | | |
|---|---|---|---|
| 2004/0087953 A1* | 5/2004 | Singhatat | A61B 17/1764 606/232 |
| 2012/0109136 A1* | 5/2012 | Bourque | A61B 17/1714 606/87 |
| 2015/0157337 A1* | 6/2015 | Wolf | A61B 17/1728 606/96 |
| 2020/0060698 A1 | 2/2020 | Woodard et al. | |
| 2021/0113223 A1 | 4/2021 | Schaumann et al. | |
| 2022/0039810 A1* | 2/2022 | Gil | A61B 17/1775 |

* cited by examiner

REUSABLE SURGICAL GUIDE FOR OSTEOSYNTHESIS SURGERY IN PARTICULAR OF THE HALLUX VALGUS

TECHNICAL FIELD

The present invention concerns the field of surgical guides and more particularly a reusable surgical guide for osteosynthesis surgery of the hallux valgus, in particular, in mini-invasive or percutaneous approach. By mini-invasive approach, it should be understood a surgery limiting the approach accesses to a few centimeters and by percutaneous approach, it should be understood a surgery limiting approach accesses to a few millimeters.

STATE OF THE ART

It is well known that the deformation of the hallux valgus results from a cuneiform-metatarsal hypermobility upon a metartarsus varus. The metatarsus varus is accentuated at the bearing phase. There is then observed an inward deviation, called varus of the first metatarsal, whereas the first phalanx, retained by its joint capsule and the sesamoidal line, deviates outwards, which is called valgus.

There are different surgical techniques allowing correcting this deformation. All these surgical techniques include at least four essential steps contributing to the durability of the correction: the lateral release of the sesamoidal line which allows releasing the retracted tissues and enables the mobilization of the first phalanx; the osteotomy of the first metatarsal (Scarf, Chevron, Bosch, . . . ) which contributes to the reduction of the angle between the first and second metatarsi and to the resection of the inflamed areas; the osteotomy of the first phalanx necessary to the recovery of the M1/P1 alignment; and the capsulorrhaphy of the joint playing a key role in holding of the correction. It should be noted that, in the percutaneous approach, this last step is irrelevant, the joint capsule being perforated a few millimeters.

In the context of a mini-invasive or percutaneous approach surgery in the correction of the hallux valgus, one amongst the commonly used techniques is called PECA (registered trademark) standing for «Percutaneous Chevron-Akin» and consists in the stabilization of the two bone fragments of the metatarsus by means of two screws inserted in parallel.

In contrast with a «Scarf» or «Chevron» hallux valgus correction, the technique differs essentially by the increase of the varus of the first metatarsus to perform the translation of the distal fragment, the DMAA standing for «Distal Metatarsal Articular Angle» then being forced. Hence, the axis of the head describes an acute angle with respect to the axis of the diaphysis of the first metatarsus.

During the surgery, the position of the first wire, the proximal wire, is the most decisive step and also the most complex to carry out. Indeed, the proper position and orientation of this wire will determine the stability of the primary mounting and also the placement of the second wire and then of the screws which will achieve the osteosynthesis.

The proximal wire shall be placed in the proximal portion of the first metatarsus, cross the two cortical portions of the bone before ending in the distal fragment made during the osteotomy and the translation. By the anatomy variety in humans, the angle of the wire differs for each individual, each osteotomy and each translation. The surgeon shall then adapt the trajectory of the proximal wire to each surgery.

A second wire, the distal wire, shall be inserted parallel to the proximal wire, with an interspace that shall be neither too large nor too small. The two wires serving as a guide for the upcoming osteosynthesis screws, the screws shall be neither too far so that both reach the distal fragment, nor too close, in order to avoid a deterioration of the screws during the insertion because of interference between the screws.

Usually, the wires insertion steps are performed under radioscopy. Hence, the X-ray images are numerous which might be harmful to the health of the patients and of the radiographers. In addition, in most cases, the wires are not parallel which results in an improper positioning of the screws, a possible mechanical weakness of the system and therefore a failure of the surgery.

In order to overcome these drawbacks, several systems allowing guiding these wires have already been imagined. It is the case in particular of the international patent application WO2017/040843 and of the American patent application US2020/0060698, commercialized, mainly by the company Wright Medical with the MICA system, a registered trademark, standing for «Mini-invasive Chevron-Akin».

The document WO2017/040843 describes chevron osteotomy tools and methods and, more particularly, an aimer guide which comprises a handle extending substantially along a longitudinal axis. The longitudinal handle delimits one or several burr hole(s) extending from a first side of the handle to a second side of the handle. A head is coupled to a distal end of the longitudinal handle. The head delimits a plurality of guide holes sized and designed so as to receive a Kirschner wire therethrough. Thus, this system consists of a single-piece guide whose distal end is inserted onto a percutaneous drill positioned beforehand at the level of the osteotomy site. Afterwards, the practitioner selects the most suited window in the proximal portion of the guide to direct his first wire based on several radiographic images. The same operation is replicated for the second wire.

Although allowing assisting the surgeon to properly direct his wires, this guide type has the drawback of not enabling an intuitive use, of not enabling the wires angle variation that is necessary to the proper translation of the epiphysis of the metatarsus and of not systematically preventing the risk of interference during the insertion of the screws. Moreover, the use of several radiographic images is still necessary.

The American patent application US2020/0060698 describes an aimer guide comprising a body defining a first guide hole sized and configured to receive a guide sleeve therethrough. The first guide hole extends through the body on a first axis. An alignment arm extends between a first end and a second end. The first end is coupled to the body. A tip extends from the second end of the alignment arm. A free end of the tip is aligned with the first axis of the first guide hole. Thus, the system is composed by a guide accompanied with guide barrels for wires. The practitioner inserts the distal end of the guide into the osteotomy and positions the touch-probe at the desired exit point of his first wire. This operation is performed again based on several radiographic images. The first barrel is positioned in the proximal area of the guide thereby allowing guiding the first wire. The same operation is replicated for the second wire. This second system allows marking the exit point of the first wire beforehand and therefore guaranteeing the trajectory while minimizing the options of parallel windows preventing the risk of interference during the insertion of the upcoming screws.

Nevertheless, its use still requires radiographic images and the defective adhesion with the metatarsal requires gestures that are complex for the practitioner in order to hold the guide in the desired position while inserting the wires.

DISCLOSURE OF THE INVENTION

Hence, one amongst the objects of the invention is to overcome these drawbacks by providing a surgical guide for osteosynthesis surgery with a simple and inexpensive design, allowing limiting the number of radiographic images, simplifying the gestures of the surgeon during the surgery and preventing the risk of interference during the insertion of the screws.

To this end, and in accordance with the invention, there is provided a reusable surgical guide for hallux valgus, forming an aimer for guiding and inserting axial wires into bone portions; said surgical guide is remarkable in that it comprises a grip constituted by a head extending at the upper end of a base, a trigger adapted to be displaced in a first slide formed in the head of the grip and whose distal end is provided with a through hole for the insertion of a wire, a blade secured to the distal end of the head of the grip, under the trigger, and a so-called aiming piece adapted to be displaced in a second slide formed in the base of the grip, said aiming piece comprising at the distal end thereof means for supporting at least one wire.

It is understood that, although the surgical guide according to the invention aims at one unique point like the surgical guides of the prior art, the guide according to the invention aims at an extrapolated unique point that is located on the moving distal fragment.

Thus, the instrumentation according to the invention adapts to the translation applied by the surgeon and therefore avoids under-corrections and over-corrections and their related problems.

According to one variant, said grip is constituted by two half-shells respectively comprising a bent head and branch whose concavity is directed towards the distal end of the trigger and whose lower end is open for the passage of the so-called aiming piece, the head and the bent branch being provided with through holes, extending opposite one another in pairs.

Preferably, the base has a circular-arc shape whose concavity is directed towards the distal end of the head of said grip.

Said base of the grip is constituted by a flat surface and two bent parallel branches, each branch being provided with at least two through holes, extending opposite one another in pairs.

Moreover, the so-called aiming piece has a circular-arc shape.

Said aiming piece has an aperture extending substantially from the proximal end up to the distal end of the aiming piece, said aperture enabling the passage of screws cooperating with the holes of the bent branches of the grip.

In addition, the means for supporting a wire are constituted by at least one cylindrical sleeve whose axis of revolution extends in the sagittal plane of the guide, in the direction of the distal end of the blade, said cylindrical sleeve forming a sheath adapted to receive a barrel for aiming a wire.

Advantageously, the sheath includes a longitudinal slot, said slot extending in the sagittal plane of said guide.

According to one variant, the means for supporting a wire are constituted by two parallel cylindrical sleeves whose axes of revolution extend in the sagittal plane of the guide, in the direction of the distal end of the blade, said cylindrical sleeves respectively forming a sheath adapted to receive a barrel for aiming a wire.

Incidentally, the trigger comprises a measuring graduation.

Moreover, said blade has an L-like general shape and comprises a proximal portion extending parallel to the head of the grip and provided with a longitudinal aperture and a distal portion adapted to bear on the epiphysis of the metatarsus.

According to one variant, said blade has a rectilinear shape and comprises a proximal portion extending parallel to the head of the grip and provided with a longitudinal aperture.

Advantageously, the surgical guide according to the invention includes means for pulling the trigger.

The means for pulling the trigger are constituted by a worm screw a first end thereof cooperates with said trigger and the opposite end thereof is provided with a knob.

Incidentally, the surgical guide according to the invention includes a rack with an unlock button to ensure translation of the head and holding of the correction.

BRIEF DESCRIPTION OF THE DRAWINGS

Other advantages and features will appear better from the following description of several variants, provided as non-limiting examples, of the surgical guide in accordance with the invention, with reference to the appended drawings wherein.

EMBODIMENT OF THE INVENTION

In the following description of the surgical guide according to the invention, the same reference numerals refer to the same elements. The different views are not necessarily plotted to scale. Moreover, the surgical guide according to the invention is particularly suited to an osteosynthesis of a hallux valgus but it is quite obvious that it could be suited to the osteosynthesis of any other portion of the anatomy of the human body yet without departing from the scope of the invention.

Figure 1:
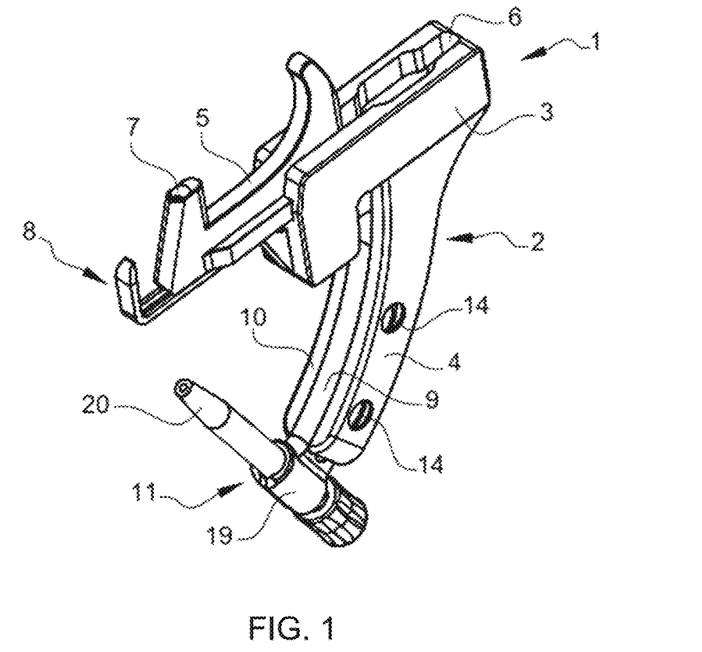
FIG. 1 is a perspective view of the surgical guide according to the invention.
Figure 2:
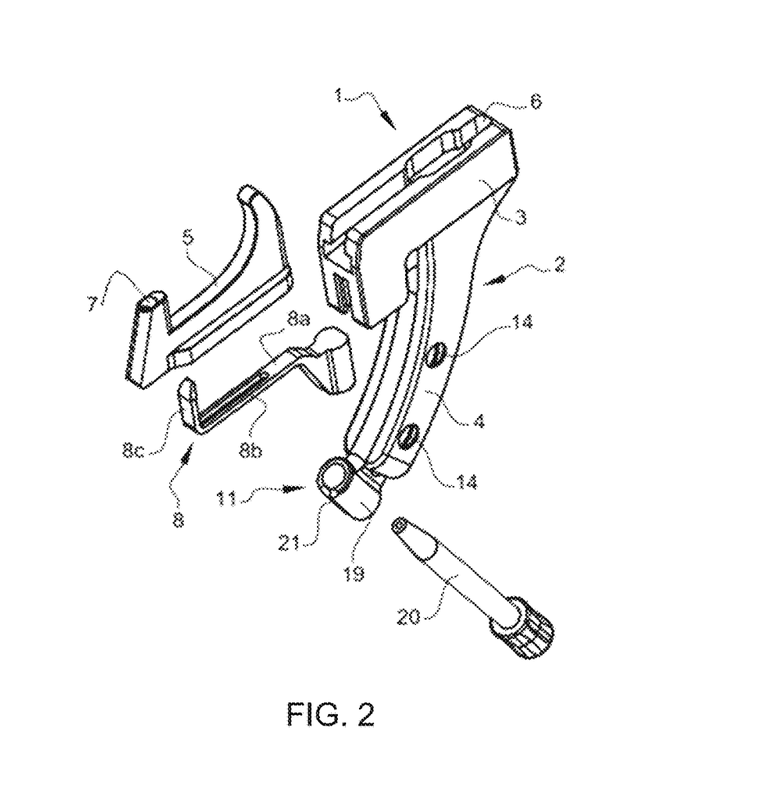
FIG. 2 is an exploded perspective view of the surgical guide according to the invention.
Figure 3:
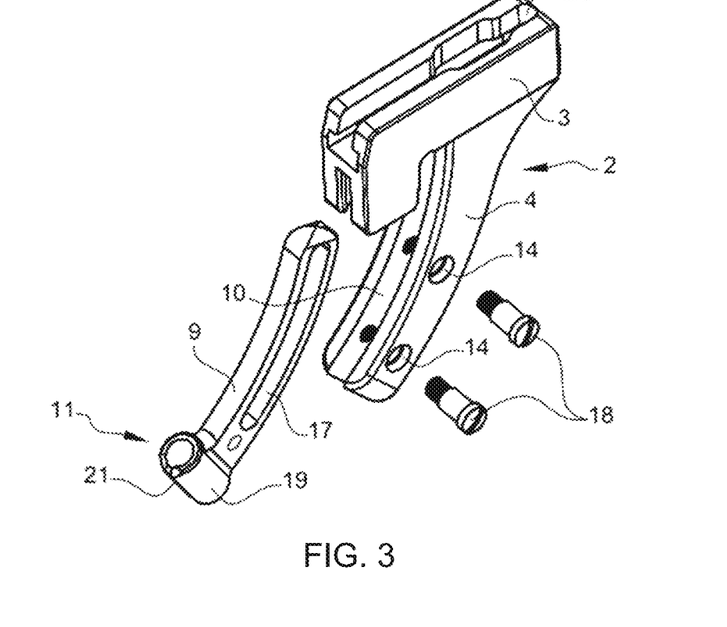
FIG. 3 is an exploded perspective view of the grip of the surgical guide according to the invention.
Figure 4:
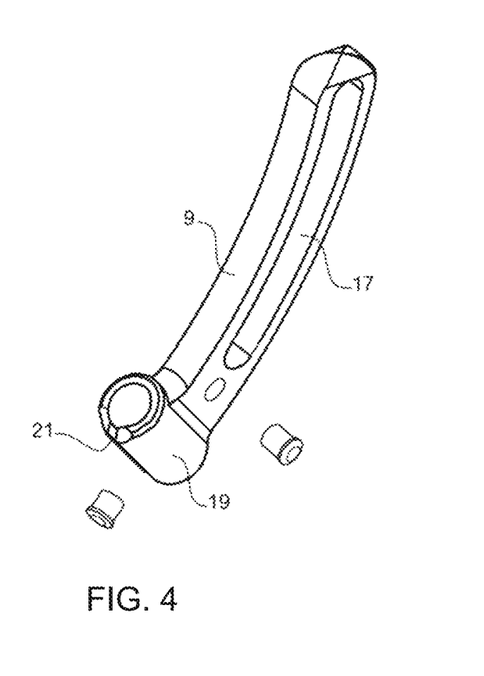
FIG. 4 is an exploded perspective view of the aiming piece sliding in the grip of the surgical guide according to the invention.
Figure 5:
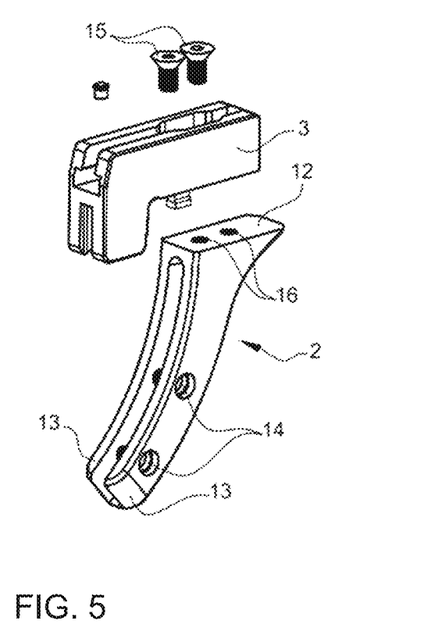
FIG. 5 is an exploded perspective view of the grip of the surgical guide according to the invention.
Figure 6:
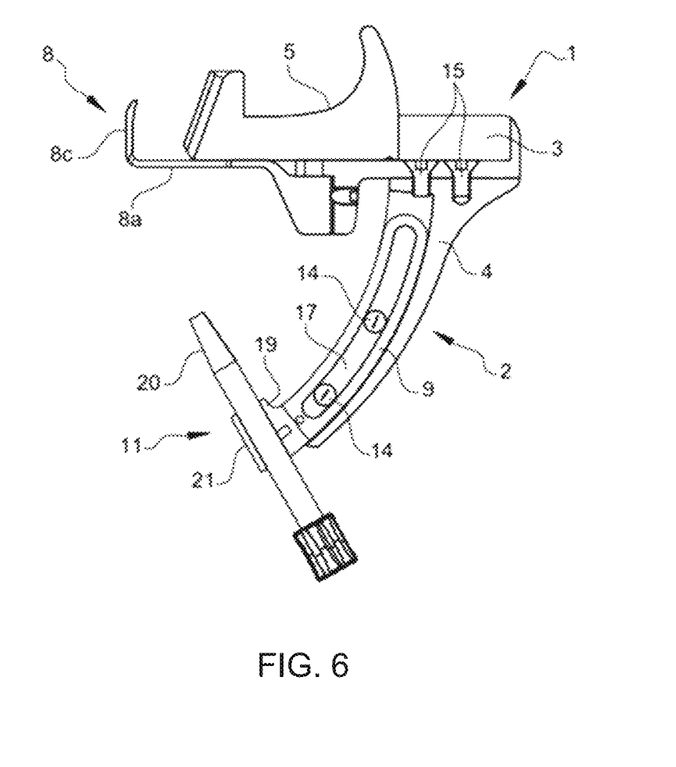
FIG. 6 is a sagittal sectional view of the surgical guide according to the invention.

Referring to FIGS. 1, 2 and 6, the surgical guide 1 according to the invention comprises a grip 2 constituted by a head 3 extending at the upper end of a base 4, a trigger 5 adapted to be displaced in a first slide 6 formed in the head 3 of the grip 2 and whose distal end is provided with a through hole 7 for the insertion of a wire, not represented in FIGS. 1 and 6, a blade 8 secured to the distal end of the head 3 of the grip 2, under the trigger 5, said blade 8 having an L-like general shape and comprising a proximal portion 8a extending parallel to the head 3 of the grip 2 and provided with a longitudinal aperture 8b and a distal portion 8c adapted to bear on the epiphysis of the metatarsus, and a so-called aiming piece 9 adapted to be displaced in a second slide 10 formed in the base 4 of the grip 2, said aiming piece 9 comprising at its distal end at least one means 11 for supporting at least one wire.

Referring to FIGS. 1 to 6, the base 4 of the grip 2 has a circular-arc shape whose concavity is directed towards the distal end of the blade 8. Said base 4 of the grip 2 is constituted by a flat surface 12 and two bent parallel branches 13, each branch 13 being provided with at least two through holes 14, extending opposite one another in pairs. The head 3, which has a substantially parallelepipedic shape, is screwed on the flat surface 12 by means of two screws 15 cooperating with two threaded holes 16 formed on said flat surface 12.

Moreover, the so-called aiming piece 9 has a circular-arc shape having the same radius of curvature as the base 4 of the grip 2. Said aiming piece has an aperture 17 extending substantially from the proximal end up to the distal end of the aiming piece 9, said aperture 17 enabling the passage of screws 18 cooperating with the holes 14 of the bent branches 13 of the grip 2.

It is quite obvious that the aiming piece 9 may have a circular-arc general shape having a radius of curvature different from the radius of curvature of the base 4 of the grip 2, the aiming piece 9 and the base 4 being nevertheless concentric, yet without departing from the scope of the invention.

In addition, the means 11 for supporting a wire are constituted by at least one cylindrical sleeve 19 whose axis of revolution extends in the sagittal plane of the surgical guide, in the direction of the distal end of the blade 8, said cylindrical sleeve 19 forming a sheath adapted to receive a barrel 20 for aiming a wire. Advantageously, the sheath formed by the cylindrical sleeve 19 includes a longitudinal slot 21, at the proximal end of the support means 11, said slot 21 extending in the sagittal plane of said guide, so as to enable an easy removal of the surgical guide after set-up of the wire, the aiming barrel being removed beforehand, the wire then passing through said slot 21.

The operation of the surgical guide according to the invention will now be explained with reference to FIGS. 7 to 13.

Figure 7:
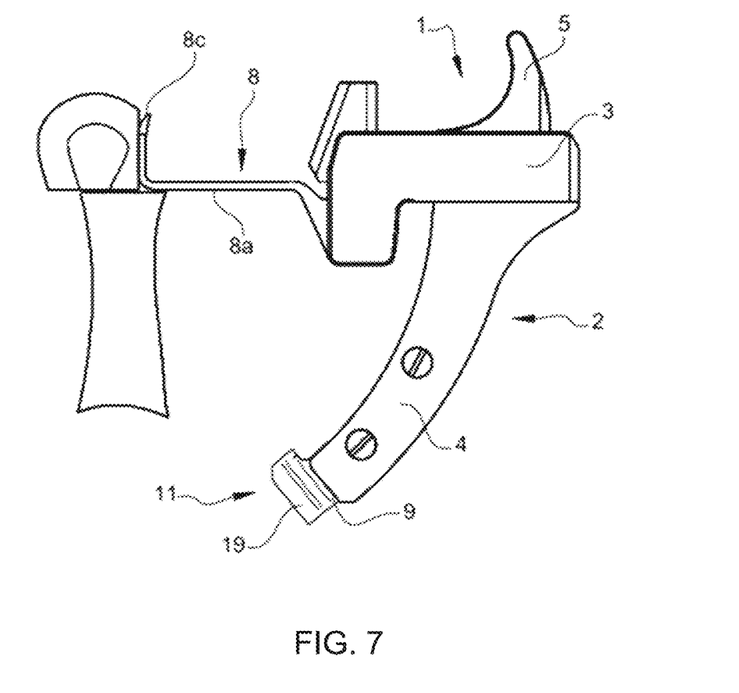
FIGS. 7 to 11 are side views of the surgical guide according to the invention at the different steps of use of said surgical guide.

The practitioner incises by about 5 mm the skin and the joint capsule at the level of the bunion. Using a percutaneous drill, he performs the medial exostectomy (FIG. 7) of the metatarsus in order to reduce the arthritic areas as much as possible. Afterwards, he will perform the osteotomy of the epiphysis of the metatarsus thereby separating the head from the diaphysis. The practitioner inserts the blade 8 into the incision such that the distal end of the blade 8 bears against the medial edge of the head of the metatarsus (FIG. 7). A slight translation is already applied during this insertion. It should be noticed that as the blade 8 is easily removable with respect to the grip 2, it could also be inserted into the incision and then mounted on the grip 2.

Figure 8:
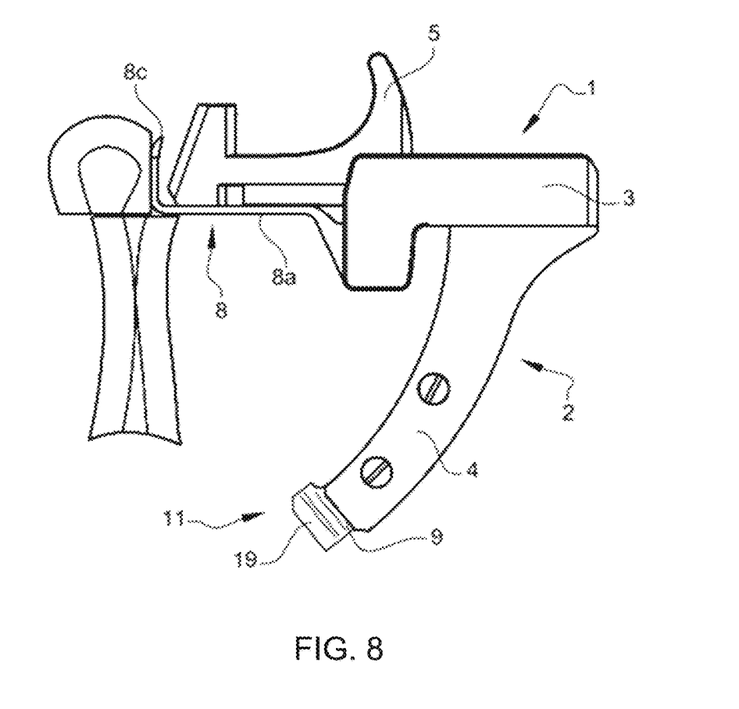
Figure 9:
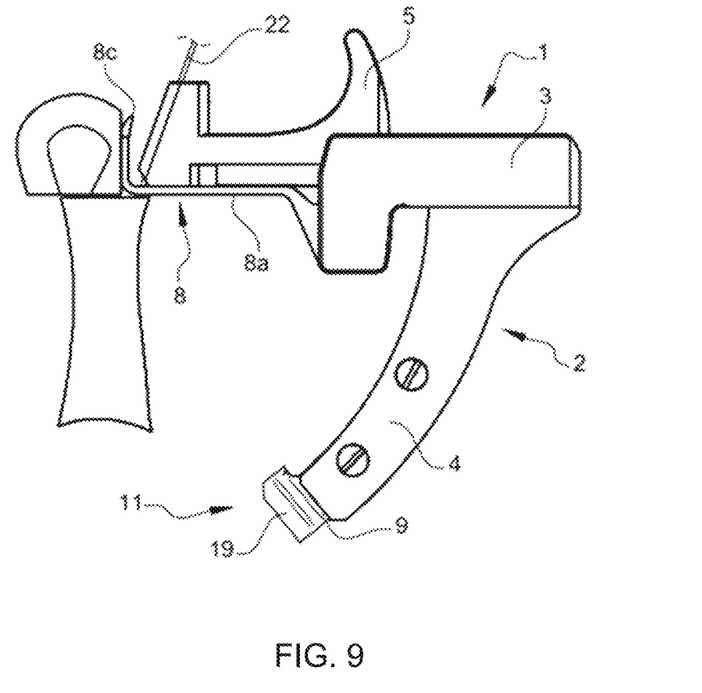

Referring to FIG. 8, the practitioner then sets the trigger 5 in position against the blade 8 by simply pressing thereon to make it slide in the first slide 6. A stabilization/draw wire 22 may then be inserted into the intramedullary canal of the metatarsus through the hole 7 of the trigger 5 provided to this end, with reference to FIG. 9.

Figure 10:
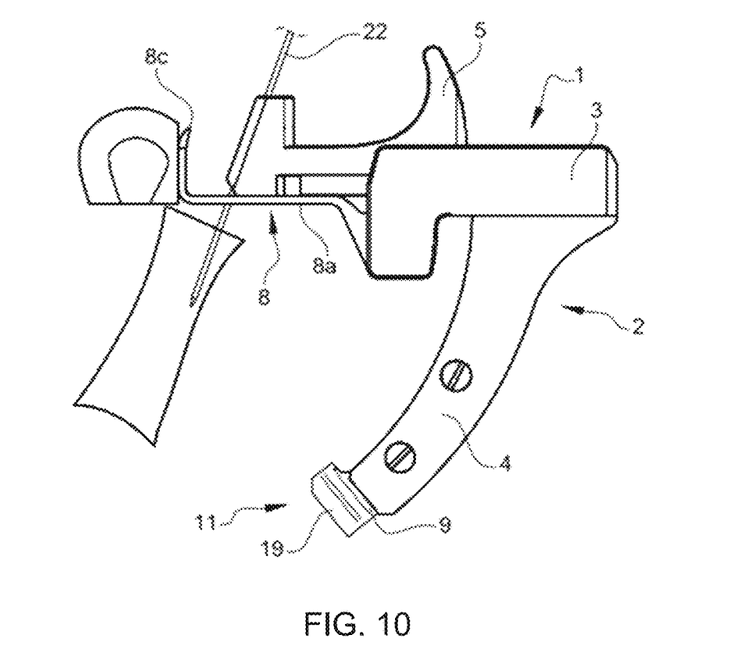

Once the draw wire 22 is set in place, with reference to FIG. 10, the practitioner could draw the diaphysis by pulling on the trigger 5. Thus, we find the principle of the surgical technique, which consists in increasing the varus of the metatarsus to translate the head. By drawing the diaphysis and holding the head of the metatarsus, a correction of the DMAA (Distal Metatarsal Articular Angle) is automatically performed.

Figure 11:
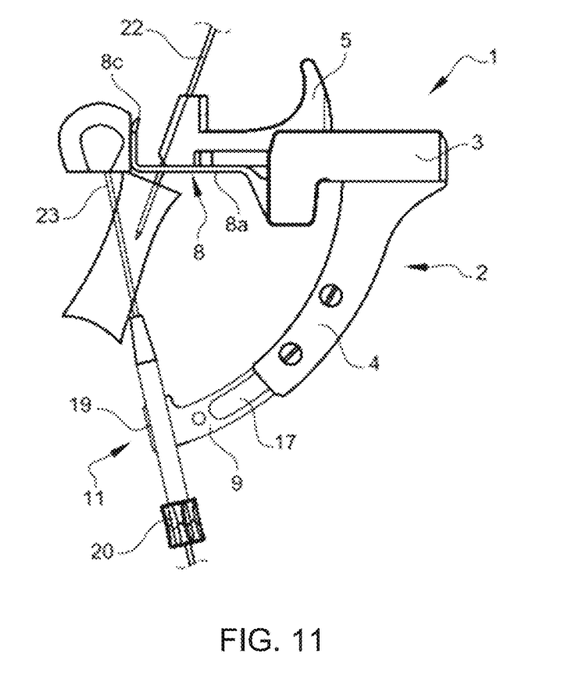
Figure 12:
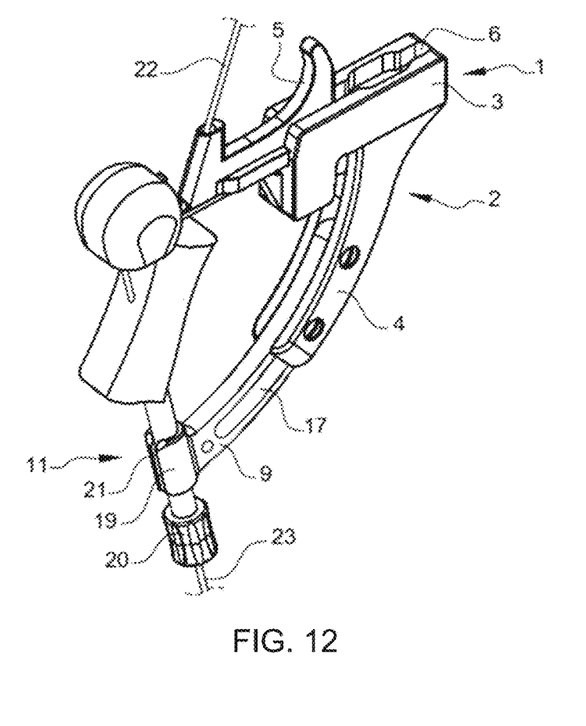
FIG. 12 is a perspective view of the surgical guide according to the invention after placement of a first wire in the first metatarsus.

Referring to FIGS. 11 and 12, by rotating the aiming piece 9, the practitioner selects the entry point of his first wire 23 which shall be as proximal as possible. He inserts the first wire and could insert the second distal wire if the device is equipped with a double sheath as will be detailed later on.

The practitioner can now remove the aiming barrel 20 used to insert the so-called proximal first wire 23, and then, by rotating the aiming piece 9, he clears the wire 23 which then passes through the slot 21 and thus extract the surgical guide according to the invention while leaving the proximal wire 23, stabilizing the system.

Figure 13:
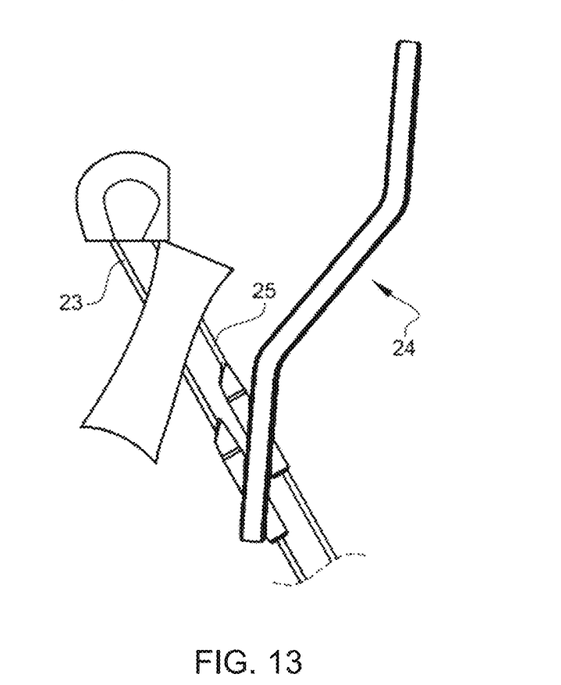
FIG. 13 is a side view of the placement of the second wire by means of a second so-called parallel guide.

Referring to FIG. 13, the practitioner may be assisted by a parallel guide 24 to insert a second wire 25, parallel to the proximal wire 23. The practitioner could, if he so wishes, insert the first implant before inserting the second wire 25. He will carry on the insertion of the second implant thereby totally fixing the system. Lastly, the practitioner will perform a last exostectomy to remove the bone wedge likely to aggress the soft tissues of the patient and hinder him when walking.

Figure 14:
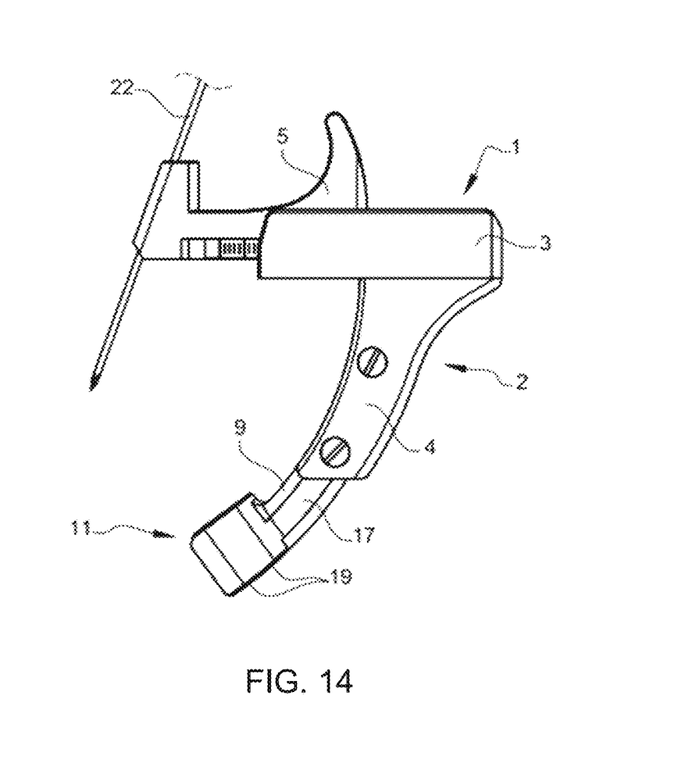
FIG. 14 is a side view of a variant of the surgical guide according to the invention.

According to one variant, with reference to FIG. 14, the surgical guide 1 according to the invention comprises, in the same manner as before, a grip 2 constituted by a head 3 extending at the upper end of a base 4, a trigger 5 adapted to be displaced in a first slide 6 formed in the head 3 of the grip 2 and whose distal end is provided with a through hole 7 for the insertion of a wire, not represented in FIGS. 1 and 6, and a so-called aiming piece 9 adapted to be displaced in a second slide 10 formed in the base 4 of the grip 2, said aiming piece 9 comprising at the distal end thereof means 11 for supporting at least one wire.

The base 4 of the grip 2 has a circular-arc shape whose concavity is directed towards the distal end of the trigger 5 of said grip 2. Said base 4 of the grip 2 is constituted by a flat surface 12 and two bent parallel branches 13, each branch 13 being provided with at least two through holes 14, extending opposite one another in pairs. The head 3, which as a substantially parallelepipedic shape, is screwed on the flat surface 12 by means of two screws 15 cooperating with two threaded holes 16 formed on said flat surface 12.

Moreover, the so-called aiming piece 9 has a circular-arc shape having the same radius of curvature as the base 4 of the grip 2. Said aiming piece has an aperture 17 extending substantially from the proximal end up to the distal end of the aiming piece 9, said aperture 17 enabling the passage of screws 18 cooperating with the holes 14 of the bent branches 13 of the grip 2.

In the same manner as before, it is quite obvious that the aiming piece 9 may have a circular-arc general shape having a radius of curvature different from the radius of curvature of the base 4 of the grip 2, the aiming piece 9 and the base 4 being nevertheless concentric, yet without departing from the scope of the invention.

The surgical guide differs from the previously-described one in that it does not include any blade 8, in that the trigger 5 comprises a measuring graduation 26 and in that the means 11 for supporting a wire are constituted by two parallel cylindrical sleeves 19 whose axes of revolution extend in the sagittal plane of the guide, in the direction of the distal end of the trigger 5, said cylindrical sleeves 19 respectively forming a sheath adapted to receive a barrel 20 for aiming a wire.

Thus, the exit point of the wire, extrapolated beforehand, is then found by measurement of the depth of the completed osteotomy. The practitioner could, if he so wishes, use a depth gauge to perform this measurement.

Figure 15:
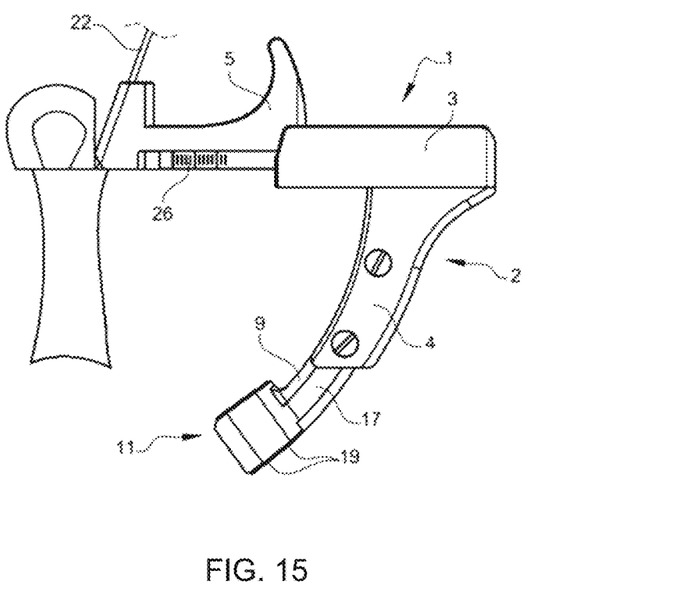
FIGS. 15 and 16 are side views of the variant of the surgical guide according to the invention at the different steps of use of said surgical guide.
Figure 16:
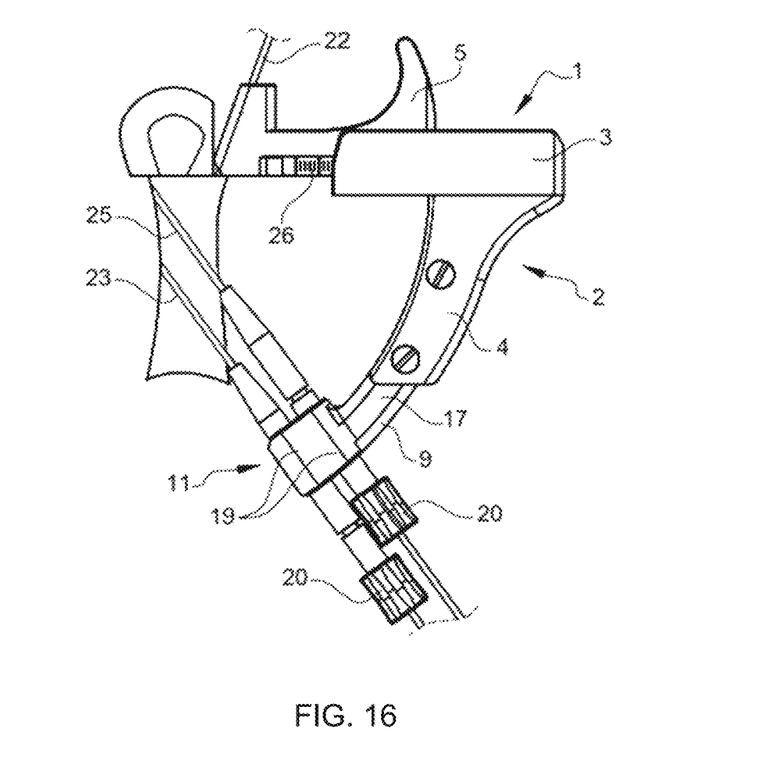

The operation of this variant of the surgical guide will now be explained with reference to FIGS. 15 and 16.

In this embodiment, the practitioner does not translate the epiphysis of the metatarsus but rather the trigger of the instrumentation according to the invention. Afterwards, the practitioner can insert the guide wire(s) using the aiming arc and a barrel attached on this arc. Hence, the use of the instrumentation according to the invention boils down, with reference to FIG. 15, to carrying out the osteotomy, measuring the depth of the osteotomy using a depth gauge, inserting the wire into the intramedullary canal of the metatarsus and performing an overlapping of the surgical guide according to the invention on the wire; then, with reference to FIG. 16, to reporting the depth measurement, inserting the screw guide wires 23, 25, removing the surgical guide, translating the epiphysis and proceeding with a complete insertion of the wires.

It should be noted that the variant represented in FIGS. 1 to 13 may include means 11 for supporting a wire constituted by two parallel cylindrical sleeves 19 whose axes of revolution extend in the sagittal plane of the guide, in the direction of the distal end of the trigger 5, said cylindrical sleeves 19 respectively forming a sheath adapted to receive a barrel 20 for aiming a wire, yet without departing from the scope of the invention.

Figure 17:
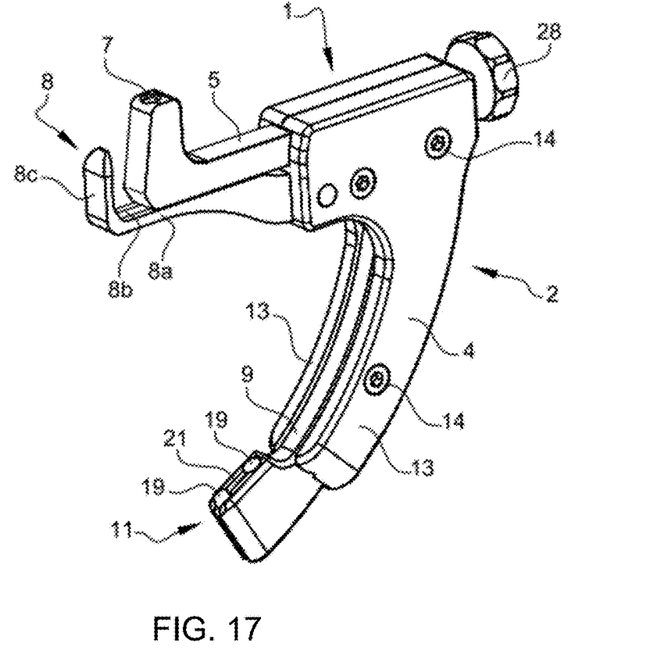
FIG. 17 is a perspective view of a second variant of the surgical guide according to the invention.
Figure 18:
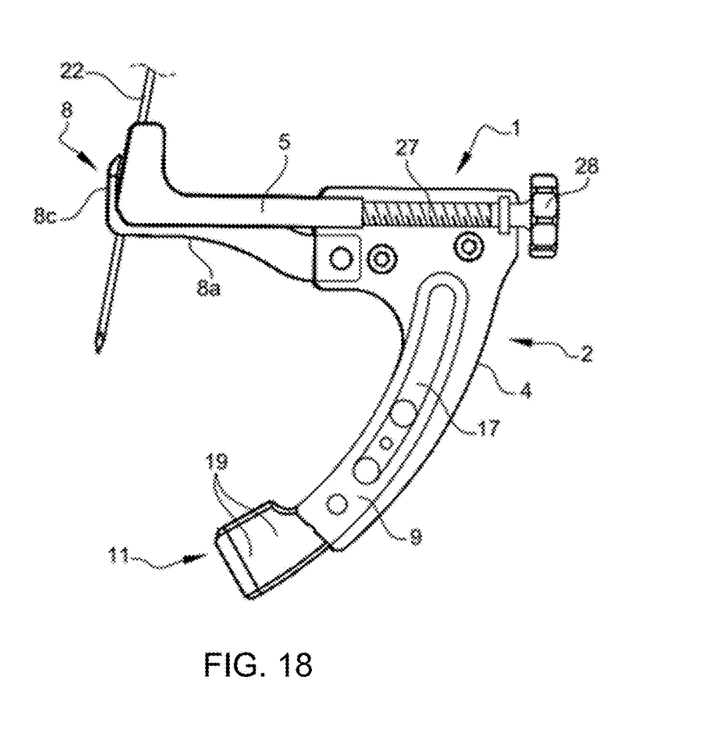
FIG. 18 is a sagittal sectional view of the second variant of the surgical guide according to the invention represented in FIG. 17.

According to a second variant, with reference to FIGS. 17 and 18, the surgical guide 1 according to the invention comprises, in the same manner as that described with reference to FIGS. 1 to 6, a grip 2 constituted by a head 3 extending at the upper end of a base 4, a trigger 5 adapted to be displaced in a first slide 6 formed in the head 3 of the grip 2 and whose distal end is provided with a through hole 7 for the insertion of a wire, not represented in the figures, a blade 8 secured to the distal end of the head 3 of the grip 2, under the trigger 5, said blade 8 having an L-like general shape and comprising a proximal portion 8a extending parallel to the head 3 of the grip 2 and provided with a longitudinal aperture 8b and a distal portion 8c adapted to bear on the epiphysis of the metatarsus, and a so-called aiming piece 9 adapted to be displaced in a second slide 10 formed in the base 4 of the grip 2, said aiming piece 9 comprising at the distal end thereof means 11 for supporting at least one wire.

Said base 4 of the grip 2 has a circular-arc shape whose concavity is directed towards the distal end of the blade 8. Said base 4 of the grip 2 is constituted by two bent parallel branches 13, each branch 13 being provided with at least two through holes 14, extending opposite one another in pairs. The head 3, which has a substantially parallelepipedic shape, is constituted by two portions, each portion of the head 3 carrying a bent 13 branch 13 forming the base 4 of the grip 2.

Moreover, the so-called aiming piece 9 has a circular-arc shape having the same radius of curvature as the base 4 of the grip 2. Said aiming piece 9 has an aperture 17 extending substantially from the proximal end up to the distal end of the aiming piece 9, said aperture 17 enabling the passage of screws 18 cooperating with a hole 14 of the bent branches 13 of the grip 2.

In the same manner as before, it is quite obvious that the aiming piece 9 may have a circular-arc general shape having a radius of curvature different from the radius of curvature of the base 4 of the grip 2, the aiming piece 9 and the base 4 being nevertheless concentric, yet without departing from the scope of the invention.

In addition, the means 11 for supporting a wire are constituted by two cylindrical sleeves 19 whose axes of revolution extend parallel to one another in the sagittal plane of the surgical guide, in the direction of the distal end of the blade 8, said cylindrical sleeves 19 forming sheaths adapted to receive a barrel for aiming a wire. Advantageously, the sheaths formed by the cylindrical sleeves 19 include a longitudinal slot 21, at the proximal end of the support means 11, said slot 21 extending in the sagittal plane of said guide, so as to enable an easy removal of the surgical guide after set-up of the wire, the aiming barrel being removed beforehand, the wire then passing through said slot 21.

The surgical guide differs from the previously-described one in that it includes means for pulling the trigger 5 constituted by a worm screw 27 a first end thereof cooperates with said trigger 5 and the opposite end thereof is provided with a knob 28. In this manner, once the translation of the head is performed by the practitioner, the surgeon has freehand to manage the dorsoplantar position of the translated epiphysis of the metatarsus. With the other hand, he can insert the wires, these therefore lying in the midplane of the head.

Incidentally, to ensure translation of the head and holding of the correction, a rack with an unlock button may be used.

Figure 19:
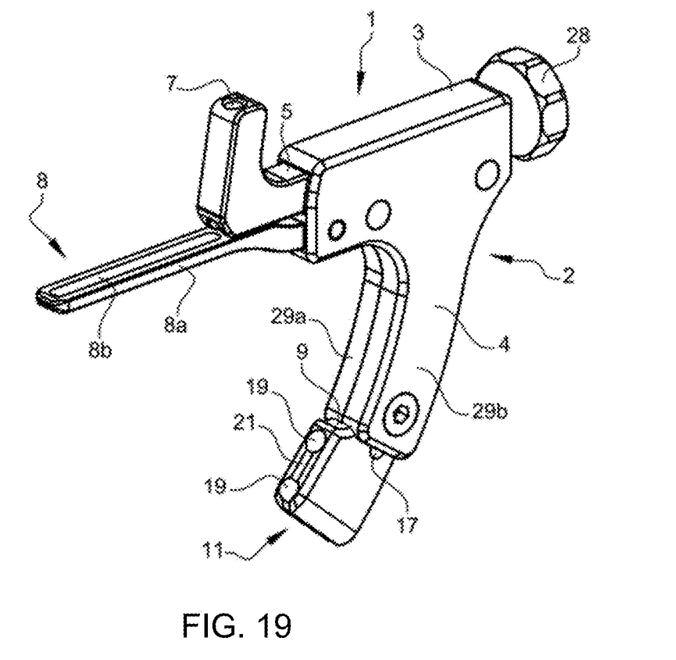
FIG. 19 is a perspective view of a third variant of the surgical guide according to the invention.
Figure 20:
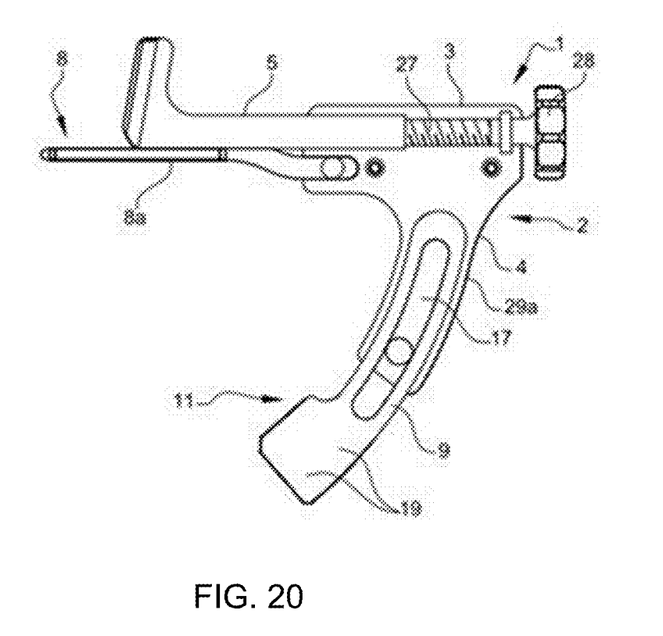
FIG. 20 is a sagittal sectional view of the third variant of the surgical guide according to the invention represented in FIG. 19.
Figure 21:
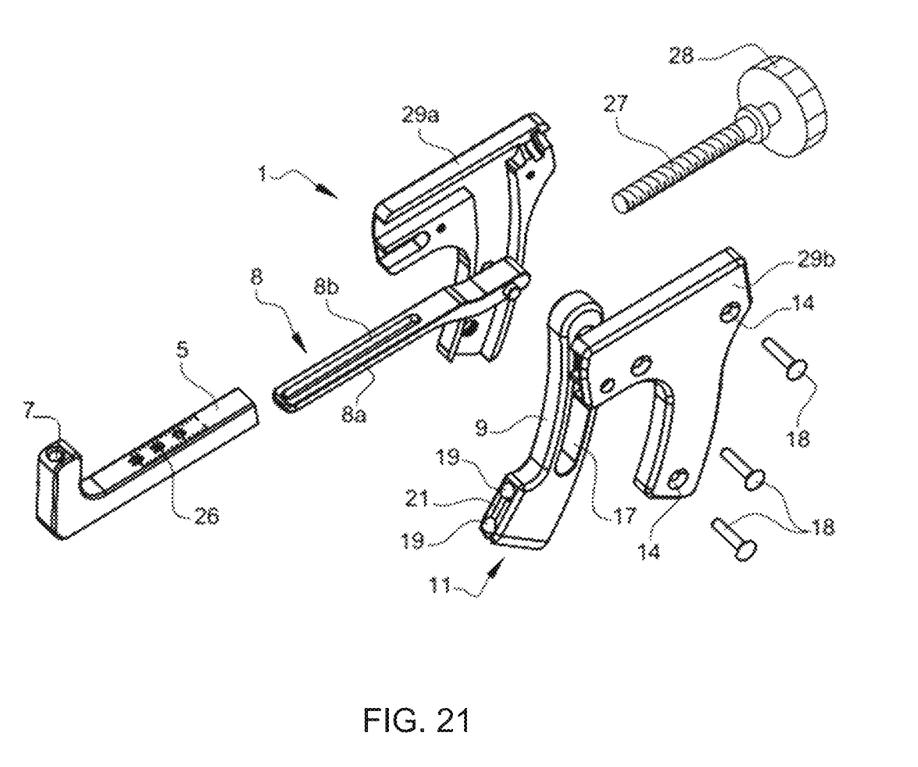
FIG. 21 is an exploded perspective view of the third variant of the surgical guide according to the invention represented in FIGS. 19 and 20.

According to a third variant, with reference to FIGS. 19 to 21, the surgical guide 1 according to the invention comprises, in the same manner as that described with reference to FIGS. 1 to 6, a grip 2 constituted by a head 3 extending at the upper end of a base 4, a trigger 5 adapted to be displaced in a first slide 6 formed in the head 3 of the grip 2 and whose distal end is provided with a through hole 7 for the insertion of a wire, not represented in the figures, a blade 8 secured to the distal end of the head 3 of the grip 2, under the trigger 5, and a so-called aiming piece 9 adapted to be displaced in a second slide 10 formed in the base 4 of the grip 2, said aiming piece 9 comprising at the distal end thereof means 11 for supporting at least one wire.

The means 11 for supporting a wire are constituted by two cylindrical sleeves 19 whose axes of revolution extend parallel to one another in the sagittal plane of the surgical guide, in the direction of the distal end of the blade 8, said cylindrical sleeves 19 forming sheaths adapted to receive a barrel for aiming a wire. Advantageously, the sheaths formed by the cylindrical sleeves 19 include a longitudinal slot 21, at the proximal end of the support means 11, said slot 21 extending in the sagittal plane of said guide, so as to enable an easy removal of the surgical guide after set-up of the wire, the aiming barrel being removed beforehand, the wire then passing through said slot 21.

In the same manner as before, the surgical guide includes means for pulling the trigger 5 constituted by a worm screw 27 a first end thereof cooperates with said trigger 5 and the opposite end thereof is provided with a knob 28. In this manner, once the translation of the head is performed by the practitioner, the surgeon has freehand to manage the dorso-plantar position of the translated epiphysis of the metatarsus. With the other hand, he can insert the wires, these therefore lying in the midplane of the head.

Incidentally, to ensure translation of the head and holding of the correction, a rack with an unlock button may be used.

The surgical guide differs from the previously-described one in that the grip 2 is constituted by two half-shells 29a and 29b respectively comprising a head 3 and a bent portion 13 whose concavity is directed towards the distal end of the trigger 5 and whose lower end is open for the passage of the so-called aiming piece 9, the flat surface 12 and the bent branch 13 being provided with through holes 14, extending opposite one another in pairs. Thus, the head 3, which has a substantially parallelepipedic shape, is formed by two half-shells 29a and 29b.

Moreover, the so-called aiming piece 9 has a circular-arc shape having the same radius of curvature as the base 4 of the grip 2. Said aiming piece 9 has an aperture 17 extending substantially from the proximal end up to the distal end of the aiming piece 9, said aperture 17 enabling the passage of screws 18 cooperating with the holes 14 of the bent branches 13 of the grip 2.

In the same manner as before, it is quite obvious that the aiming piece 9 may have a circular-arc general shape having a radius of curvature different from the radius of curvature of the base 4 of the grip 2, the aiming piece 9 and the base 4 being nevertheless concentric, yet without departing from the scope of the invention.

The surgical guide also differs from the previously-described one in that said blade 8 has a rectilinear general shape rather than an L-like shape, and thus comprising only a proximal portion 8a extending parallel to the head 3 of the grip 2 and provided with a longitudinal aperture 8b.

Moreover, it shall be emphasized that, regardless of the embodiment of the surgical guide according to the invention, the latter enables an accurate insertion of the first proximal wire and that, regardless of the anatomy of the first metatarsus, an insertion of the second distal wire parallel to the first proximal wire, without any risk of interference between the screws, a symmetrical use of the surgical guide according to the invention and a reduced use of radiographic images.

Finally, it is quite obvious that the examples that have just been provided are only particular illustrations that are not restrictive with regards to the fields of application of the invention.

The invention claimed is:

1. A reusable surgical guide for osteosynthesis surgery, the reusable surgical guide forming an aimer for guiding and inserting axial wires into bone portions, the reusable surgical guide comprising:
    a grip comprising:
        a base, and
        a head that is attached to an end of the base and extends along a longitudinal axis from a proximal end to a distal end, the head including a first slide extending in a direction from the proximal end to the distal end of the head;
    a slidable member adapted to slide in the first slide along the direction from the proximal end to the distal end of the head of the grip, wherein the slidable member comprises a distal end that includes a through hole for insertion of a wire, and an axis of the through hole in the distal end of the slidable member is transverse to the longitudinal axis;
    a blade secured to the distal end of the head of the grip and extending in continuation of the head along a direction that is parallel to the longitudinal axis of the head, the blade being secured adjacent to the slidable member; and
    an aiming piece adapted to be displaced in a second slide formed in the base of the grip, said aiming piece comprising at a distal end thereof at least one sleeve for supporting at least one wire.

2. The surgical guide according to claim 1, wherein the base has a circular-arc shape having a concavity directed towards the distal end of the head of said grip.

3. The surgical guide according to claim 2, wherein the base of the grip comprises a flat surface and two bent parallel branches, each bent parallel branch including at least two through holes, extending opposite one another in pairs.

4. The surgical guide according to claim 1, wherein the aiming piece has a circular-arc shape.

5. The surgical guide according to claim 1, wherein the aiming piece has an aperture extending substantially from a proximal end to the distal end of the aiming piece, said aperture enabling passage of screws cooperating with holes in bent branches of the grip.

6. The surgical guide according to claim 1, wherein the at least one sleeve has an axis that extends in a sagittal plane of the surgical guide and in a direction towards a distal end of the blade, said at least one sleeve being adapted to receive a barrel for aiming the at least one wire.

7. The surgical guide according to claim 6, wherein the at least one sleeve includes a longitudinal slot, said longitudinal slot extending in the sagittal plane of said surgical guide.

8. The surgical guide according to claim 6, wherein the at least one sleeve includes a first through hole and a second through hole that is parallel to the first through hole, the first through hole and the second through hole having axes that extend in the sagittal plane of the surgical guide and in the direction towards the distal end of the blade, the first through hole being adapted to receive a first barrel for aiming a first wire, and the second through hole being adapted to receive a second barrel for aiming a second wire.

9. The surgical guide according to claim 1, wherein the slidable member comprises a measuring graduation.

10. The surgical guide according to claim 1, wherein said blade has an L-like general shape and comprises:
    a proximal portion extending parallel to the head of the grip and including a longitudinal aperture, and
    a distal portion adapted to bear on an epiphysis of a metatarsus.

11. The surgical guide according to claim 1, wherein said blade has a rectilinear shape and comprises a proximal portion extending parallel to the head of the grip and including a longitudinal aperture.

12. The surgical guide according to claim 1, further comprising a means for pulling the slidable member.

13. The surgical guide according to claim 12, wherein the means for pulling the slidable member comprises a screw, the screw including a first end that cooperates with said slidable member and an opposite end that is provided with a knob.

14. The surgical guide according to claim 1, wherein the blade extends from the distal end of the head in a distal direction in continuation of the head.

15. The surgical guide according to claim 14, wherein the proximal end of the head is attached to the end of the base.

16. The surgical guide according to claim 1, wherein an opening to the first slide is formed in the distal end of the head such that the slidable member can slide in a distal direction along the longitudinal axis to extend beyond the distal end of the head in the distal direction.

17. A reusable surgical guide for osteosynthesis surgery, the reusable surgical guide forming an aimer for guiding and inserting axial wires into bone portions, the reusable surgical guide comprising:
 a grip comprising a head extending at an end of a base, the head extending along a longitudinal axis from a proximal end to a distal end;
 a slidable member adapted to be displaced in a first slide formed in the head of the grip, wherein the slidable member comprises a distal end that includes a through hole for insertion of a wire, and an axis of the through hole in the distal end of the slidable member is transverse to the longitudinal axis;
 a blade secured to the distal end of the head of the grip and extending in continuation of the head, the blade being secured adjacent to the slidable member, the blade being stationary in relation with the head when the blade is secured to the head; and
 an aiming piece adapted to be displaced in a second slide formed in the base of the grip, said aiming piece comprising at a distal end thereof at least one sleeve for supporting at least one wire.

18. A reusable surgical guide for osteosynthesis surgery, the reusable surgical guide forming an aimer for guiding and inserting axial wires into bone portions, the reusable surgical guide comprising:
 a grip comprising a head extending at an end of a base, the head extending along a longitudinal axis from a proximal end to a distal end;
 a slidable member adapted to be displaced in a first slide formed in the head of the grip, wherein the slidable member comprises a distal end that includes a through hole for insertion of a wire, and an axis of the through hole in the distal end of the slidable member is transverse to the longitudinal axis;
 a blade secured to the distal end of the head of the grip and extending in continuation of the head, the blade being secured adjacent to the slidable member; and
 an aiming piece adapted to be displaced in a second slide formed in the base of the grip, said aiming piece comprising at a distal end thereof at least one sleeve for supporting at least one wire,
 wherein the at least one sleeve has an axis that extends in a sagittal plane of the surgical guide and in a direction towards a distal end of the blade, said at least one sleeve being adapted to receive a barrel for aiming the at least one wire.

* * * * *